United States Patent
Angeles et al.

(10) Patent No.: US 10,028,956 B2
(45) Date of Patent: Jul. 24, 2018

(54) METHODS OF TREATING VARIOUS CANCERS USING AN AXL/CMET INHIBITOR IN COMBINATION WITH OTHER AGENTS

(71) Applicant: Ignyta, Inc., San Diego, CA (US)

(72) Inventors: Thelma S. Angeles, West Chester, PA (US); Mark A. Ator, Paoli, PA (US); Mangeng M. Cheng, Stoughton, PA (US); Bruce Dorsey, Ambler, PA (US); Robert L. Hudkins, Chester Springs, PA (US); Bruce A. Ruggeri, West Chester, PA (US)

(73) Assignee: IGNYTA, INC., San Diego, CA (US)

( * ) Notice: Subject to any disclaimer, the term of this patent is extended or adjusted under 35 U.S.C. 154(b) by 0 days.

(21) Appl. No.: 14/907,514

(22) PCT Filed: Jul. 31, 2014

(86) PCT No.: PCT/US2014/049028
§ 371 (c)(1),
(2) Date: Jan. 25, 2016

(87) PCT Pub. No.: WO2015/017607
PCT Pub. Date: Feb. 5, 2015

(65) Prior Publication Data
US 2016/0184309 A1 Jun. 30, 2016

Related U.S. Application Data

(60) Provisional application No. 61/861,482, filed on Aug. 2, 2013.

(51) Int. Cl.
| | |
|---|---|
| *A61K 31/497* | (2006.01) |
| *A61K 31/535* | (2006.01) |
| *A61K 31/54* | (2006.01) |
| *A61K 31/513* | (2006.01) |
| *A61K 45/06* | (2006.01) |
| *A61K 31/517* | (2006.01) |
| *A61K 31/541* | (2006.01) |
| *A61K 31/47* | (2006.01) |

(52) U.S. Cl.
CPC .......... *A61K 31/513* (2013.01); *A61K 31/517* (2013.01); *A61K 45/06* (2013.01); *A61K 31/47* (2013.01); *A61K 31/541* (2013.01)

(58) Field of Classification Search
CPC ..... A61K 31/517; A61K 31/541; A61K 31/47
USPC .............................. 514/228.22, 234.5, 252.17
See application file for complete search history.

(56) References Cited

U.S. PATENT DOCUMENTS 5,747,498 A * 5/1998 Schnur ................. C07D 231/12
514/233.8
5,770,599 A * 6/1998 Gibson ................. C07D 403/12
514/228.2

FOREIGN PATENT DOCUMENTS

WO WO 13/074633 5/2013
WO WO 2013074633 A1 * 5/2013 ........... C07D 401/12

OTHER PUBLICATIONS

Puri et al., 2008, Synergism of EGFR and c-Met pathways, cross-talk and inhibition, in non-small cell lung cancer, Journal of Carcinogenesis, 7:9.
International Search Report and Written Opinion dated Nov. 13, 2014 in PCT/US14/049028.
International Preliminary Report on Patentability dated Feb. 11, 2016 in PCT/US14/049028.
J A Friedman: Abstract C272 : Antitumor activity of the dual AXL/c-Met in hibitor CEP-48783 in Champions primary Tumor Graft (TM) models of human non-small cell lung cancer (NSCLC). Molecular Cancer Therapeutics, 2013 p. C272, XP855337343 *abstract* (3 pages).
S. Miknyoczki: Abstract C275: CEP-40783: A potent and selective AXL/c-Met inhibitor for use in breast, non-small cell lung (NSCLC), and pancreatic cancers. Molecular Cancer Therapeutics, Mol Cancer Ther, vol. 12, No. IIS, 2013 Oct. 19, 2013), p. C275, XP055337340, *abstract* (4 pages).
Tang, et al. Dual MET-EGFR combinatorial inhibition against T790M-EGFR-mediated erlotinib-resistant lung cancer. British Journal of Cancer. Sep. 16, 2008;99(6):911-22.
Zhang, et al. Activation of the AXL kinase causes resistance to EGFR-targeted therapy in lung cancer. Nat Genet. Jul. 1, 2012;44(8):852-60.

* cited by examiner

*Primary Examiner* — Kevin E Weddington
(74) *Attorney, Agent, or Firm* — Foley & Lardner LLP

(57) ABSTRACT

This application describes the use of the compound (I) or a salt thereof, either alone or in combination with other therapeutically active agents, for the treatment of particular cancers, including any solid or hematological cancer in which AXL or c-Met is over-expressed.

(I)

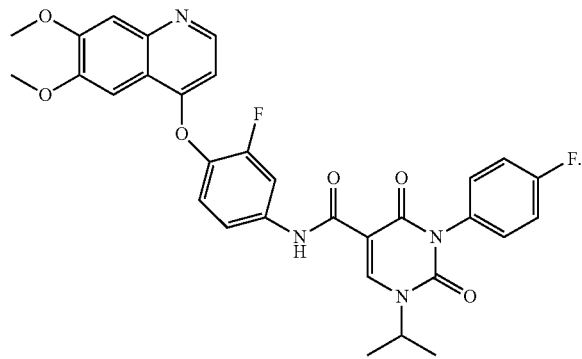

8 Claims, 11 Drawing Sheets

CEP-40783 Inhibits AXL and c-Met Phosphorylation in Tumor Xenografts

A. *In vivo* H1299 AXL tumor PK/PD

B. *In vivo* GTL-16 c-Met tumor PK/PD

METHODS OF TREATING VARIOUS CANCERS USING AN AXL/CMET INHIBITOR IN COMBINATION WITH OTHER AGENTS

This application is a National Stage Entry of PCT International Application No. PCT/US2014/049028, filed Jul. 31, 2014, which claims the benefit of U.S. Provisional Application No. 61/861,482, filed Aug. 2, 2013, each of which are incorporated herein by reference in its entirety, including any drawings.

BACKGROUND

The present application relates to novel compounds that are inhibitors of the receptor tyrosine kinases AXL and c-MET. The compounds are suitable for treatment of AXL or c-MET-mediated disorders such as cancer, and the development of resistance to cancer therapies.

Receptor tyrosine kinases (RTKs) are transmembrane proteins that transduce signals from the extracellular environment to the cytoplasm and nucleus to regulate normal cellular processes, including survival, growth, differentiation, adhesion, and mobility. Abnormal expression or activation of RTKs has been implicated in the pathogenesis of various human cancers, linked with cell transformation, tumor formation and metastasis. These observations have led to intense interest in the development of tyrosine kinase inhibitors as cancer therapeutics (Rosti et al, Crit. Rev. Oncol. Hematol. 2011. [Epub ahead of print]; Gorden et al, J. Oncol. Pharm. Pract. 2011. [Epub ahead of print]; Grande et al, Mol. Cancer Ther. 2011, 10, 569).

AXL is a member of the TAM (TYRO3, AXL, MER) receptor tyrosine kinase (RTK) family originally identified as a transforming gene expressed in cells from patients with chronic myelogenous leukemia (O'Bryan et. al Mol. Cell Biol. 1991, 11, 5016) or chronic myeloproliferative disorder (Janssen et. al Oncogene, 1991, 6, 2113). AXL activation occurs by binding of its cognate protein ligand, growth arrest specific 6 (Gash), homotypic dimerization through its extracellular domain or cross-talk via the interleukin (IL)-15 receptor or HER2. AXL signaling stimulates cellular responses, including activation of phosphoinositide 3-kinase-Akt, extracellular signal-regulated kinase (ERK) and p38 mitogen-activated protein kinase cascades, the NF-κB pathway, and signal transducer and activator of transcription (STAT) signaling (Hafizi et. al Cytokine Growth Factor Rev., 2006, 17, 295). Numerous biological consequences of AXL signaling, including invasion, migration, survival signaling, angiogenesis, resistance to chemotherapeutic and targeted drugs, cell transformation, and proliferation, represent undesirable traits associated with cancer (Linger et al. Adv. Cancer Res., 2008, 100, 35; Hafizi et. al Cytokine Growth Factor Rev., 2006, 17, 295; Holland et al, Cancer Res. 2005, 65, 9294).

AXL receptors regulate vascular smooth muscle homeostasis (Korshunov et al, Circ. Res. 2006, 98, 1446) and are implicated in the control of oligodendrocyte cell survival (Shankar et al, J. Neurosci. 2003, 23, 4208). Studies in knockout mice have revealed that TAM receptors play pivotal roles in innate immunity by inhibiting inflammation in macrophages and dendritic cells (Sharif et al, J. Exp. Med. 2006, 203, 1891; Rothlin et al, Cell. 2007, 131, 1124), promoting the phagocytosis of apoptotic cells (Lu et al, Nature. 1999, 398, 723; Lu & Lemke, Science. 2001, 293, 306; Prasad et al, Mol. Cell Neurosci. 2006, 3, 96) and stimulating the differentiation of natural killer cells (Park et al, Blood 2009, 113, 2470).

AXL has been found to be constitutively activated due to gene amplification and/or altered protein expression (O'Bryan et al, J. Biol. Chem. 1995, 270, 551; Linger et al, Expert Opin. Ther. Targets. 2010, 14, 1073; Mudduluru et al, Oncogene, 2011, 30, 2888). Altered expression of AXL has been reported in a variety of human cancers (Crosier et al, Leuk. Lymphoma. 1995, 18, 443; Challier et al, Leukemia, 1996, 10, 781; Ito et al, Thyroid. 1999, 9, 563; Sun et al, Oncology. 2004, 66, 450; Green et al, Br. J. Cancer. 2006, 94, 1446; Liu et al, Blood. 2010, 116, 297) and is associated with invasiveness and metastasis in lung cancer (Shieh et al, Neoplasia. 2005, 7, 1058), prostate cancer (Shiozawa et al, Neoplasia. 2010, 12, 116), breast cancer (Zhang et al, Cancer Res. 2008, 68, 1905), esophageal cancer (Hector et al, Cancer Biol. Ther. 2010, 10, 1009), ovarian cancer (Rankin et al, Cancer Res. 2010, 70, 7570), pancreatic cancer (Koorstra et al, Cancer Biol. Ther. 2009, 8, 618; Song et al, Cancer, 2011, 117, 734), liver cancer (He et al, Mol. Carcinog. 2010, 49, 882), gastric cancer (Wu et al, Anticancer Res. 2002, 22, 1071; Sawabu et al, Mol Carcinog. 2007, 46, 155), thyroid cancer (Avilla et al, Cancer Res. 2011, 71, 1792), renal cell carcinoma (Chung et al, DNA Cell Biol. 2003, 22, 533; Gustafsson et al, Clin. Cancer Res. 2009, 15, 4742) and glioblastoma (Hutterer et al, Clin. Cancer Res. 2008, 14, 130).

Indeed, AXL overexpression is associated with late stage and poor overall survival in many of those human cancers (Rochlitz et al, Leukemia, 1999, 13, 1352; Vajkoczy et al, Proc Natl. Acad. Sci. 2006, 103, 5799). AXL contributes to at least three of the six fundamental mechanisms of malignancy in human, by promoting cancer cell migration and invasion, involving in tumor angiogenesis, and facilitating cancer cell survival and tumor growth (Holland et al, Cancer Res. 2005, 65, 9294; Tai et al, Oncogene. 2008, 27, 4044; Li et al, Oncogene, 2009, 28, 3442; Mudduluru et al, Mol. Cancer Res. 2010, 8, 159). AXL is strongly induced by epithelial-to-mesenchymal transitions (EMT) in immortalized mammary epithelial cells and AXL knockdown completely prevented the spread of highly metastatic breast carcinoma cells from the mammary gland to lymph nodes and several major organs and increases overall survival (Gjerdrum et al, Proc. Natl. Acad. Sci. USA. 2010, 107, 1124; Vuoriluoto et al, Oncogene. 2011, 30, 1436), indicating AXL represents a critical downstream effector of tumor cell EMT requiring for cancer metastasis.

AXL is also induced during progression of resistance to therapies including imatinib in gastrointestinal stromal tumors (Mahadevan et al, Oncogene. 2007, 26, 3909) and Herceptin and EGFR inhibitor therapy (e.g. lapatinib) in breast cancer (Liu et al, Cancer Res. 2009, 69, 6871) via a "tyrosine kinase switch", and after chemotherapy in acute myeloid leukemia (Hong et al, Cancer Lett. 2008, 268, 314). AXL knockdown was also reported to lead to a significant increase in chemosensitivity of astrocytoma cells in response to chemotherapy treatment (Keating et al, Mol. Cancer Ther. 2010, 9, 1298). These data indicate AXL as an important mediator for tumor resistance to conventional chemotherapy and molecular-based cancer therapeutics.

The c-MET receptor was initially identified as the TPR-MET oncogene in an osteosarcoma cell line treated with a chemical carcinogen. The TPR-Met protein is able to transform and confer invasive and metastatic properties to non-tumorigenic cells (Sattler et. al, Current Oncology Rep., 2007, 9, 102). The oncogenic potential is a result of spontaneous dimerization and constitutive activation of TPR-MET. Aberrant expression of HGF and c-MET is associated with the development and poor prognosis of a wide range of solid tumors, including breast, prostate, thyroid, lung, stomach, colorectal, pancreatic, kidney, ovarian, and uterine carcinoma, malignant glioma, uveal melanoma, and osteo- and soft-tissue sarcoma (Jaing et. al Critical Rev. Oncol/Hematol., 2005, 53, 35). Gastric tumors with an amplification of the wt-c-MET gene are more susceptible to MET inhibition, thereby making c-MET an attractive target (Smolen et. al Proc. Natl. Acad. Sci. USA, 2006, 103, 2316).

In vitro and in vivo studies have shown that increased and dysregulated c-MET activation leads to a wide range of biological responses associated with the malignant phenotype. These responses include increased motility/invasion, increased tumorigenicity, enhanced angiogenesis, protection of carcinoma cells from apoptosis induced by DNA-damaging agents such as adriamycin, ultraviolet light, and ionizing radiation, and enhanced rate of repair of DNA strand breaks [Comoglio et. al J. Clin. Invest., 2002, 109, 857, Sattler et. al Current Oncology Rep., 2007, 9, 102; Fan et. al, Mol. Cell Biol., 2001, 21, 4968). Based upon these data, HGF may enhance mutagenicity following DNA damage, allowing tumor cells with genetic damage to survive, and thus leading to resistance to chemo- and radiotherapeutic treatment regimens (Fan et. al, Mol. Cell Biol., 2001, 21, 4968; Hiscox et. al Endocrine-Related Cancer, 2004, 13, 1085).

MET amplification plays a unique critical role in mediating resistance of non-small cell lung cancer to EGFR inhibitors (e.g. Tarceva™, Iressa™, Tykerb™) the resistance of HER2 positive breast cancer to trastuzumab (Sattler et. al, Update Cancer Ther., 2009, 3, 109; Engleman et. al, Science, 2007, 316, 1039, Shattuck et. al Cancer Res., 2008, 68, 1471, Agarwal et. al, Br. J. Cancer, 2009, 100, 941; Kubo et. al, Int. J. Cancer 2009, 124, 1778) Inhibition of c-MET in Tarceva™ or Iressa™ resistant cells using shRNA or small molecules alone or in combination with an EGFR inhibitor overcame MET-mediated resistance to EGFR inhibitors [Agarwal et. al, Br. J. Cancer, 2009, 100, 941; Bachleitner-Hoffman et. al, Mol. Cancer Ther., 2008, 7, 3499, Tang et. al, Br. J. Cancer, 2008, 99, 911; Bean et. al, Proc. Natl. Acad. Sci. USA, 2007, 104, 20932). Due to the pleiotropic, pro-tumorigenic activities of the HGF-c-MET axis, inhibiting this pathway would be predicted to have potent anti-tumor effects in many common cancers through multiple complimentary mechanisms.

SUMMARY

The present application describes the use of a particular AXL/c-Met inhibitor, CEP-40783, or a salt thereof, either alone or in combination with other therapeutically active agents, for the treatment of particular cancers, including any solid or hematological cancer in which AXL or c-Met is over-expressed. The structure of CEP-40783 is shown below:

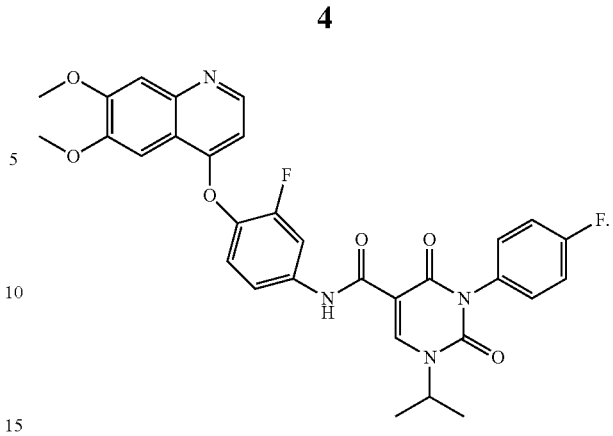

BRIEF DESCRIPTIONS OF THE DRAWINGS

DESCRIPTION

Figure 1:
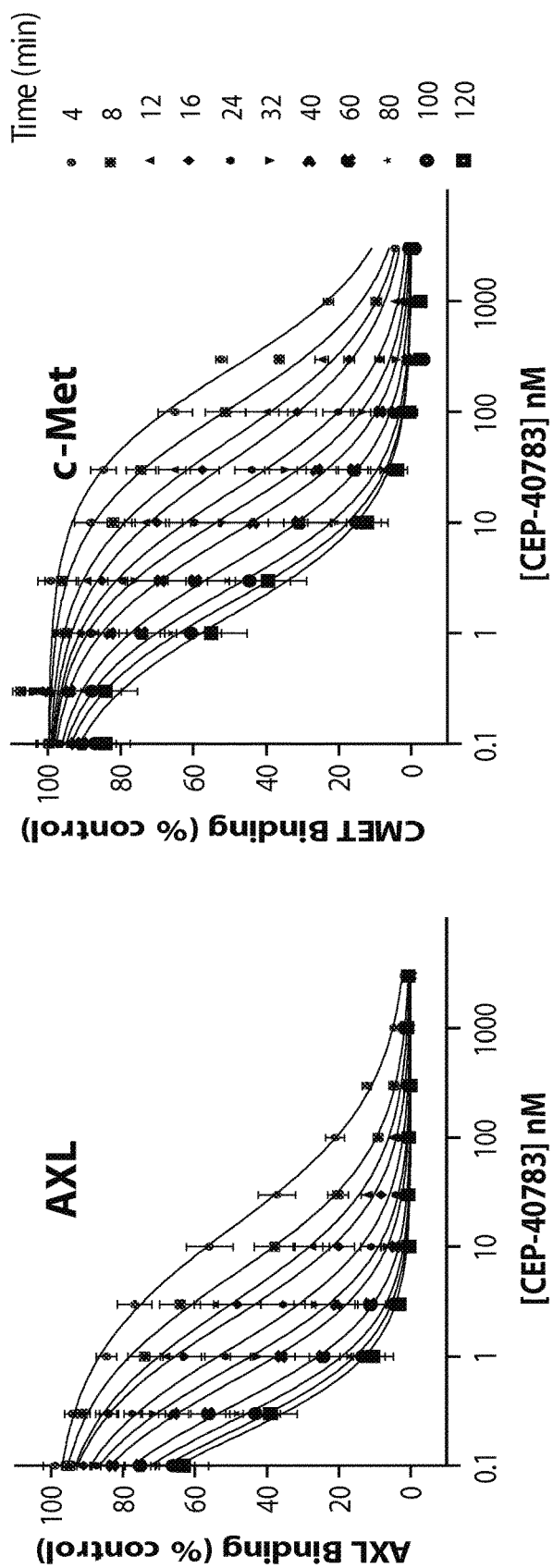
FIG. 1 depicts the binding assay data for CEP-40783 inhibition of AXL and c-Met.

As used herein, the following terms have the meanings ascribed to them below unless specified otherwise.

The term "about" refers to ±10% of a given value.

"Pharmaceutical composition" refers to a composition having a safety and/or efficacy profile suitable for administration to a subject, including a human.

"Pharmaceutically acceptable" when used by itself or in conjunction with another term or terms refers to materials, such as, for example, an active ingredient, salt, excipient, carrier, vehicle, or diluent that is generally chemically and/or physically compatible with the other ingredients comprising a formulation, and/or is generally physiologically compatible with the recipient thereof.

"Subject" refers to a member of the class Mammalia. Examples of mammals include, without limitation, humans, primates, chimpanzees, rodents, mice, rats, rabbits, horses, livestock, dogs, cats, sheep, and cows.

"Therapeutically effective amount" refers to an amount of a compound sufficient to improve or inhibit the worsening or severity of one or more symptoms associated with a particular disorder or condition that is being treated in a particular subject or subject population. It should be appreciated that the determination or selection of the dosage form(s), dosage amount(s), and route(s) of administration is within the level of ordinary skill in the pharmaceutical and medical arts.

"Treatment" refers to the acute or prophylactic diminishment or alleviation of at least one symptom or characteristic associated with or caused by a disorder being treated. For example, treatment can include diminishment of a symptom of a disorder or complete eradication of either a symptom and/or the disorder itself. It should be understood that the terms "preventing" and "preventative" and "prophylactic" are not absolute but rather refer to uses and results where the administration of a compound or composition diminishes the likelihood or seriousness of a condition, symptom, or disease state, and/or may delay the onset of a condition, symptom, or disease state for a period of time. In some embodiments, the terms "treating", "treated", and "treatment" refer to curative uses and results as well as uses and results that diminish or reduce the severity of a particular condition, symptom, disorder, or disease described herein.

As used herein, the terms "therapeutically active agent" and "therapeutic agent", whether used alone or in conjunction with another term or terms, refers to any compound, i.e. a drug or a salt thereof, that may be or has been found to be useful in the treatment of a particular condition, symptom, disease or disorder and is not CEP-40783.

The compounds (including CEP-40783 and/or any other therapeutically active agent) described herein may be isolated and used per se as a free base or may be isolated in the form of a salt. It should be understood that the terms "salt(s)" and "salt form(s)" whether used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more. Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved (by a regulatory authority such as FDA) for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one aspect, the present application provides a compound that is

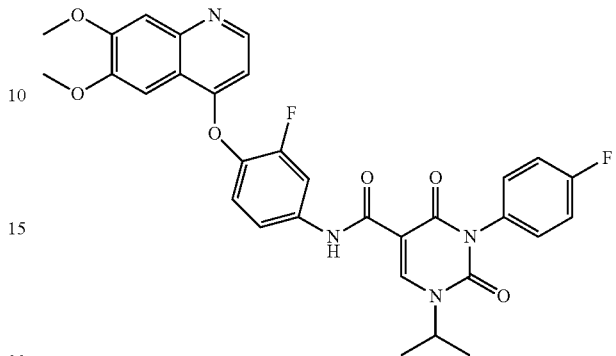

or a salt thereof. The compound can be referred to by the chemical name 3-(4-Fluorophenyl)-1-isopropyl-2,4-dioxo-1,2,3,4-tetrahydropyrimidine-5-carboxylic acid [4-(6,7-dimethoxyquinolin-4-yloxy)-3-fluorophenyl]-amide and is also known as CEP-40783.

In another aspect, the present application provides for methods of treatment of various cancers including any solid or hematological cancer in which AXL or c-Met is over-expressed, where the method comprises the administration of CEP-40783 or a pharmaceutically acceptable salt thereof to a subject in recognized need of such treatment. In another aspect, the present application provides for the use of CEP-40783 or a pharmaceutically acceptable salt thereof in the preparation of a medicament for treating a solid or hematological cancer in which AXL or c-Met is over-expressed, wherein the medicament is subsequently administered to a subject in recognized need thereof. Preferably, CEP-40783 or a pharmaceutically acceptable salt thereof is administered to the subject in a pharmaceutical composition that comprises a pharmaceutically acceptable excipient.

In another aspect, the application describes methods of treating particular cancers including, but not limited to, non small cell lung cancer (NSCLC), breast cancer, gastric cancer and pancreatic cancer using CEP-40783 or a pharmaceutically acceptable salt thereof. In some embodiments the cancer is NSCLC that is resistant or insensitive to treatment with EGFR inhibitors. In some embodiments, CEP-40783 or a pharmaceutically acceptable salt thereof, is administered as a single agent. In other embodiments CEP-40783, or a pharmaceutically acceptable salt thereof, is administered in combination with another therapeutic agent. In some embodiments the other therapeutic agent is erlotinib. In still other embodiments the other therapeutic agent is gefitinib.

In any of the aforementioned methods of treatment (or medical uses) the solid or hematological cancer in which AXL or c-Met is over-expressed may be treated prophylactically, acutely or chronically using CEP-40783 or a salt thereof. In some embodiments, CEP-40783 or a salt thereof may be used in combination with another therapeutic agent. In some embodiments CEP-40783 or a pharmaceutically acceptable salt thereof is administered simultaneously with the other therapeutic agent. In other embodiments CEP-40783 or a pharmaceutically acceptable salt thereof is administered sequentially, i.e., administered before or after the other therapeutic agent. In such embodiments, the CEP- 40783 or a pharmaceutically acceptable salt thereof is administered after the subject exhibits some degree of resistance or insensitivity to treatment with another therapeutic agent. In some embodiments, the other therapeutic agent is erlotinib. In still other embodiments the other therapeutic agent is gefitinib.

In the therapeutic applications described herein, CEP-40783 or a pharmaceutically acceptable salt thereof, can be administered in a wide variety of oral and/or parenteral dosage forms. In one embodiment, the compounds of the present invention are delivered orally. Parenteral administration should be understood as administration by injection, that is, intravenously, intramuscularly, intracutaneously, subcutaneously, intraduodenally, or intraperitoneally. In certain embodiments, the compounds of the present invention are administered intravenously or subcutaneously. Also, the compounds described herein can be administered by inhalation, for example, intranasally. Additionally, the compounds of the present invention can be administered transdermally. The compounds can also be delivered rectally, bucally or by insufflation.

Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. For example in some embodiments CEP-40783 or a salt thereof is administered from one to four times per day. A typical dose is about 1 mg to about 1,000 mg, such as about 5 mg to about 500 mg. In certain embodiments, the typical dose is about 1 mg to about 300 mg, such as about 5 mg to about 250 mg. In still other embodiments, the typical dose is about 10 mg to 100 mg. In some embodiments CEP-40783 or a salt thereof is dosed relative to body weight. For example, in some embodiments CEP-40783 or a salt thereof is administered in an amount of about 0.1 mg/kg to about 500 mg/kg, such as about 1 mg/kg to about 100 mg/kg, or to about 5 mg/kg to about 75 mg/kg. In some embodiments CEP-40783 or a salt thereof is administered in an amount of about 10 mg/kg to about 55 mg/kg.

CEP-40783 can be prepared using any number of different methods, including, for example, using the methods described in WO 2013/0074633.

Biology

CEP-40783 is an orally active, potent and selective AXL and c-Met kinase inhibitor, with enzyme $IC_{50}$ values of 7 nM and 12 nM, respectively. In AXL-transfected 293GT cells, CEP-40783 was 27-fold more active compared to recombinant enzyme with an $IC_{50}$ value of 0.26 nM. Comparably high cellular potency was observed in NCI-H1299 human NSCL cells ($IC_{50}$=0.1 nM). CEP-40783 also demonstrated superior activity against c-Met in GTL-16 cells ($IC_{50}$=6 nM). The increased inhibitory activity of CEP-40783 in cells may be due to its extended residence time on both AXL and c-Met, consistent with a Type II mechanism. The prolonged residence time of CEP-40783 at the target may provide for improved in vivo efficacy, selectivity and therapeutic index. Additionally, CEP-40783 showed high kinome selectivity against 298 kinases with an S90 of 0.04 (fraction of kinases showing >90% inhibition at 1 µM).

A summary of PK data across various species is presented in Table 1 below:

TABLE 1

| Parameters | Rat[a] | Dog[b] | Monkey[b] |
|---|---|---|---|
| % F | 57 | 100 | 77 |
| $C_{max}$ (ng/mL) | 593 | 1172 | 260 |
| $AUC_{0-t}$ (ng h/mL; p.o.) | 16334 | 14429 | 3030 |
| $t_{1/2}$ i.v. (h) | 21.5 | 27.6 | 14.5 |
| CL (mL/min/kg) | 1.4 | 0.5 | 2.2 |
| $V_d$ (L/kg) | 2.6 | 1.3 | 1.2 |

[a]Administered at 1 mg/kg i.v. and 3 mg/kg p.o.
[b]Administered at 0.5 mg/kg i.v. and p.o.

CEP-40783 Demonstrates Time-Dependent Binding Kinetics for Inhibition of AXL and c-Met Time-dependent binding assays were performed in Greiner low volume white 384-well plates. Assay buffer consisted of 50 mM Hepes (pH 7.5), 10 mM $MgCl_2$, 1 mM EGTA, and 0.01% Brij-35, while compound dilution buffer contained 1% DMSO in assay buffer. Compound dilution buffer (5 µL) was added to the assay plate. Serial half-log dilutions of CEP-40783 were prepared in DMSO at 150× final assay concentration in a 384-well polypropylene plate and 100 µL transferred robotically to the assay plate. Kinase tracer (5 µL; Invitrogen PV5592) was added to all the wells. The final tracer concentration was 10 nM AXL and 100 nM for c-Met. LanthaScreen Eu-anti-GST antibody (5 µL of 6 nM, 2 nM final; Invitrogen PV5594) was added to DMSO (no inhibitor) control wells while the remaining wells received 5 µL of the same antibody plus 15 nM GST-tagged enzyme (5 nM final). Kinetic readings were immediately initiated on an EnVision™ 2104 plate reader (PerkinElmer) fitted with a laser light source (337 nm), a Lance/DELFIA dual mirror, and APC (665 nm) and europium (615 nm) filters. Thirty readings were taken at 4-min intervals and the 665 nm/615 nm emission ratio was calculated. The average ratio corresponding to the no enzyme control was subtracted from all the data Inhibition curves for compounds were generated by plotting percent control activity versus log 10 of the concentration of compound. $IC_{50}$ values were calculated by nonlinear regression using the sigmoidal dose-response (variable slope) equation in XLfit The fold-shift in $IC_{50}$ was calculated by dividing the initial value by the lowest value obtained, and the time the maximal change was observed was also recorded (tmax).

When tested using a LanthaScreen™ Eu-kinase binding assay CEP-40783 displayed time-dependent binding kinetics for AXL and c-Met which is consistent with a Type II mechanism (See FIG. 1). The binding data shows a 35-fold shift in the $IC_{50}$ value in CEP-40783 inhibition of AXL from time $t_0$ to $t_{max}$ of 2 hrs. CEP-40783 also displayed time-dependent inhibition of c-Met in which a 38-fold shift in the $IC_{50}$ was noted.

Dissociation of CEP-40783 from AXL and c-Met

Rates of dissociation of CEP-40783 from AXL and c-Met were also determined using the LanthaScreen™ Eu-kinase binding assay. Assay buffer was prepared as for association, and used for all dilutions. A 5-µL aliquot of 80 nM LanthaScreen Eu-anti-GST antibody:20 nM GST-tagged enzyme mix was added to the Greiner low volume white 384-well plate, with antibody only added to control wells. Compound (100 nL) in DMSO was added by pintool at 2000-fold over the final assay concentration. DMSO was added to no inhibitor control wells. After a one-hour incubation at ambient temperature to allow formation of the enzyme-inhibitor complex, 2 µL of the reaction mix was transferred to a 384 Optiplate (PerkinElmer) and 78 µL of kinase tracer 236 was added. The final tracer concentration was 100 nM for AXL and 200 nM for c-Met. Readings were immediately initiated and total of 60 time points were taken at 2-min intervals, at 25° C. or 37° C. The background subtracted ratio was normalized to the no inhibitor control to calculate the % tracer bound, which was plotted with respect to time. The data was fitted to the one phase association model in GraphPad Prism (La Jolla Calif.).

Figure 2:
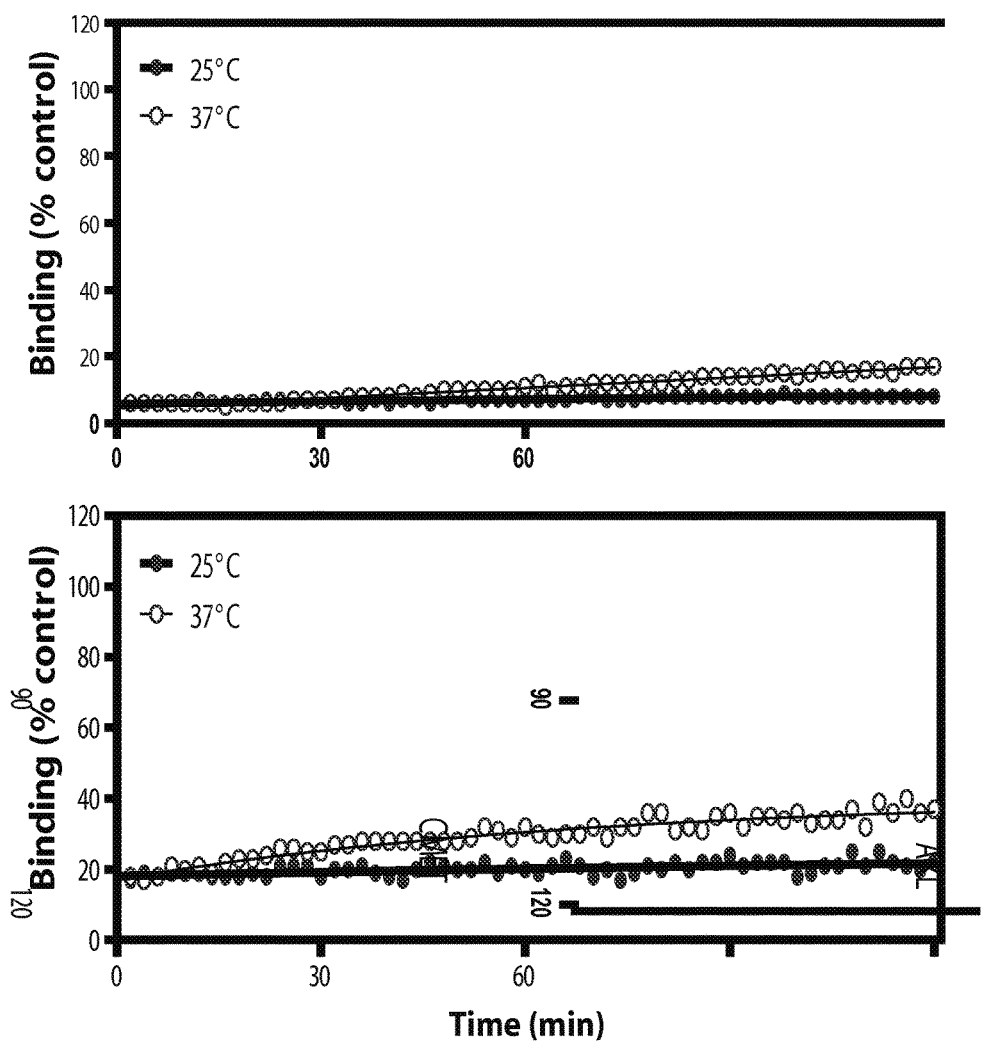
FIG. 2 depicts dissociation rate data of CEP-40783 from AXL and c-Met.

As seen in FIG. 2 CEP-40783 displays very slow "off-rates" for AXL and c-Met at 25° C., which is illustrative of pseudo-irreversible binding kinetics. The dissociation rates were slightly enhanced by higher temperature (37° C.). It is believed that the potent AXL and c-Met cellular activities of CEP-40783 can be explained by the slow dissociation rates, which results in prolonged drug-receptor residence times. Type I kinase inhibitors have been shown to exhibit rapid dissociation rates using this technology.

CEP-40783 Inhibits AXL and c-Met Phosphorylation in Tumor Xenografts

Female Nu/Nu mice (6-8 weeks, Charles River Laboratory, Wilmington, Mass.) were maintained 5/cage in microisolator units on a standard laboratory diet (Teklad Labchow, Harlan Teklad, Madison, Wis.). Animals were housed under humidity- and temperature-controlled conditions and the light/dark cycle was set at 12-hour intervals. Mice were quarantined at least 1 week prior to experimental manipulation. Experiments were approved (Protocol 03-023) by the Institutional Animal Care and Use Committee of Teva Pharmaceuticals Inc Briefly, NCI-H1299 NSCL cells (for AXL studies) or GTL-16 gastric carcinoma cells (for c-Met studies) were collected and resuspended in DMEM medium at density of $5 \times 10^7$/mL and an aliquot (100 µL) of the cell suspension ($5 \times 10^6$ cells) was inoculated subcutaneously to the left flank of each mouse with a 23 g needle. When the tumor xenograft volumes reached approximately 300-500 mm$^3$ the mice received a single oral administration of either PEG-400 vehicle or indicated doses of CEP-40783 at 100 µL/dose. At indicated time points post dosing, the mice (3 mice at each time point) were sacrificed by decapitation and blood was collected in 1.5 mL microcentrifuge tubes containing 20 µL of heparin sodium (10,000 unit/mL in H$_2$O, Cat#0210193191, MP Biomedical, Solon, Ohio) and left on ice briefly. The tubes were centrifuged at 20,817×g (Eppendorf Centrifuge 5417R with a FA45-30-11 rotor) for 8 minutes at 4° C. and the plasma was collected and transferred to 1.5 mL microfuge tubes, which were then stored at −80° C. The tumors were excised and weighed, cut into small pieces with a scalpel and placed into a round-bottom 14 mL tube (Cat#352059, Becton Dickinson, Franklin, N.J.) on ice. Two volumes of FRAK lysis buffer without detergent [10 mM Tris, pH 7.5, 50 mM sodium chloride, 20 mM sodium fluoride, 2 mM sodium pyrophosphate, 0.1% BSA, plus freshly prepared 1 mM activated sodium vanadate, 4 mM DTT, 1 mM PMSF and the protease inhibitor cocktail III (1:100 dilution, Cat#539134, Calbiochem, La Jolla, Calif.)] were added to 1 volume of tumor (eg, 500 µL FRAK lysis buffer were added to 250 mg tissue). The tissues were then disrupted with a hand-held tissue blender for 2-3 cycles, 10-15 seconds each cycle with 1-2 minute interval. The lysates were then sonicated twice, 4-5 strokes each time. The tissue lysates were transferred to 1.5 mL microfuge tubes and centrifuged at 20,817×g (Eppendorf Centrifuge 5417R with a FA45-30-11 rotor) for 10 minutes at 4° C. The supernatants (12 µL) were transferred to 1.5 mL microcentrifuge tubes containing 108 µL FRAK lysis buffer and 40 µL of 4×LDS sample buffer (Cat# NP0007, Invitrogen) with freshly added 100 nM dithiotreitol (Cat# F820-02, JT Baker, Phillipsburg, N.J.). The remaining supernatants were stored at −80° C. The compound levels in both plasma and tumor lysates were measured by LC-MS/MS. Immunoblot analyses of phospho-c-Met and total c-Met, and phosphor-AXL and total AXL for tumor PD analyses were carried out according to the protocols provided by the antibody suppliers (Cell Signaling Technology). The rabbit phospho-c-Met (Y1234/1235) (Cat#3129) and c-Met antibodies (Cat#3127) and rabbit phospho-AXL (Y702) (Cat#5724) and AXL antibodies (Cat#4939) were purchased from Cell Signaling Technology (Beverly, Mass.). The samples were heat-inactivated at 90° C. for 5 minutes; 20 µL of each sample was resolved by NuPAGE 7% Tris-acetate gels (Cat# EA03552Box, Invitrogen) at 150 V until the dye front was out of the gels. The gels were transferred to nitrocellulose membranes (Cat# LC2000, Invitrogen) for 2 hours at 30V constant using a wet XCell II blot module (Cat# EL9051, Invitrogen). The membranes were blocked in Tris-buffered saline (TBS) containing 0.2% Tween-20 (TBST) and 3% Nestlé Carnation nonfat milk (Nestle USA Inc, Solon, Ohio) at room temperature (RT) for 1 hour. The membranes were incubated with anti-phospho-c-Met (Tyr1234/1235) or anti-phospo AXL antibody (Tyr702; diluted 1:1000 in TBST containing 3% bovine serum albumin) for 1.5 hours at RT or overnight at 40° C. while rocking gently. After washing 3 times with TBST for 10 minutes each time, the membranes were incubated with goat-anti-rabbit antibody conjugated with horseradish peroxidase (HRP) (Cat# W401B, Promega, Madison, Wis.) diluted in TBST containing 3% nonfat-milk for 1 hour at RT while rocking gently. After washing 3 times with TBST for 10 minutes each time and one time with TBS for 5 minutes, the membranes were incubated with 5 mL of ECL™-Western blotting detection reagents (Cat# RPN2106, GE Healthcare UK, Buckinghamshire, UK) for 5 minutes and exposed to Kodak chemiluminescence BioMax films (Cat#178, 8207; Carestream Health Inc, Rochester, N.Y.) for visualization. The membranes were then stripped by incubating with stripping buffer (62.5 mM Tris HCl pH 6.8, 2% SDS and 100 mM 2-mercaptoethanol) for 30 minutes at 56° C., and re-blotted with anti-c-Met and anti-AXL antibody and then goat anti-rabbit-HRP secondary antibody diluted 1:10,000. The films imaging individual bands of phospho- and total AXL and phospho- and total c-Met were scanned (HP Scanjet 7400c, Hewlett-Packard Company, Palo Alto, Calif.) and quantified with Gel-Pro Analyzer software (Media Cybernetics, Inc, Bethesda, Md.). The magnitude of normalized AXL and normalized c-Met phosphorylation of each tumor sample relative to vehicle control tumor samples was then calculated.

In PK/PD studies, CEP-40783 showed dose- and time-dependent inhibition of AXL phosphorylation using NCI-H1299 NSCL xenografts with ~80% target inhibition at 0.3 mg/kg 6 h post dose and complete target inhibition to >90% inhibition at 1 mg/kg between 6-24 h, while a 10 mg/kg po dose resulted in complete AXL inhibition up to 48 h post dosing. Female Scid mice bearing NCI-H1299 NSCLC were administered CEP-40783 as indicated and plasma and tumor samples were collected at 6 hrs post-administration (FIG. 3A). Effects on phospho-AXL (Cell Signaling #5724) and total AXL (Cell Signaling #4977) in tumor samples were detected by immunoblotting and the magnitude of inhibition of normalized AXL phosphorylation was calculated.

Figure 3:
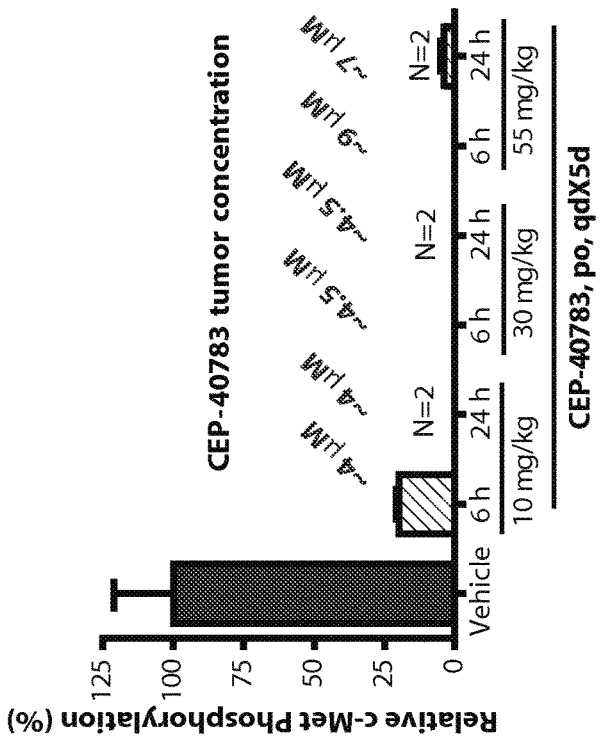
FIG. 3A depicts the effects on AXL phosphorylation in female SCID mice bearing NCI-H1299 NSCLC xenografts after oral administration of CEP-40873.
FIG. 3B depicts the effects on c-Met phosphorylation in nu/nu mice bearing GLT-16 gastric carcinoma subcutaneous tumorgrafts after oral administration of CEP-40873.
Figure 3:
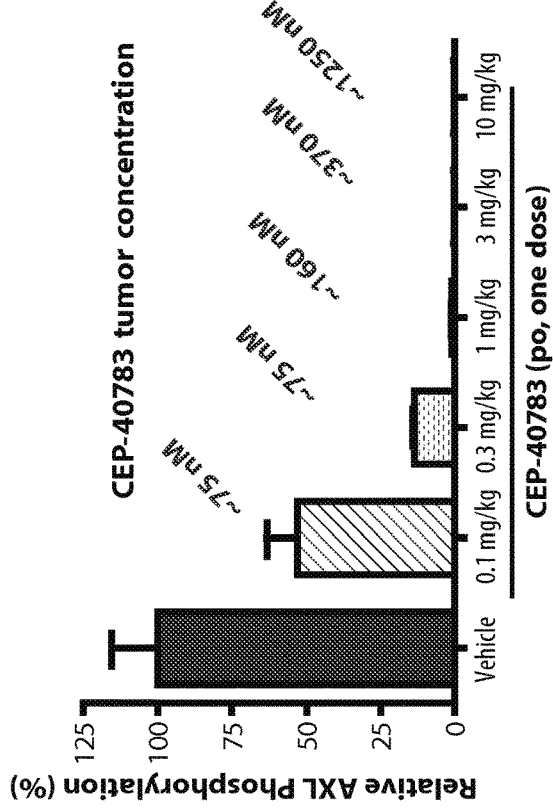

Nu/nu mice bearing GTL-16 gastric carcinoma sc tumor xenografts were dosed were dosed as indicated and plasma and tumor samples were collected 6 and 24 hrs post dose (FIG. 3 B). Effects on c-Met phosphorylation were determined using ELISA (Invitrogen KH00281 and KH02031) and the magnitude of inhibition of normalized c-Met phosphorylation was calculated.

CEP-40783 Inhibits the Growth of NIH3T3/AXL Xenografts

The engineered NIH3T3/AXL cell line was generated as follows. The human AXL cDNA was subcloned into the pQCXIP vector and the sequences were confirmed by sequencing at Children's Hospital of Philadelphia. PT67 cells ($5\times10^5$) in 4 mL DMEM+10% FBS were seeded in each well of 6-well plates (Cat#353046, Becton Dickinson, Franklin Lakes, N.J.) and cultured at 37° C. in a humidified incubator with 5% $CO_2$ overnight. The cells were transfected with 2 µg of pQCXIP-AXL with Lipofectamine™ 2000 (Cat#52887, Invitrogen, Carlsbad, Calif.) transfection reagent per the manufacturer's protocol. In brief, the DNA in 500 µL culture media was mixed with 500 µL media containing 20 µL Lipofectamine™ 2000 transfection reagent, and the mixture was incubated at room temperature for 20 minutes. After the culture media was aspirated and the dishes were washed with 2 mL 1× Dulbecco's Phosphate Buffered Saline (PBS, Cat#21-031-CM, Mediatech, Manassas, Va.), 1 mL of the appropriate transfection mixture was added to each well. The wells were returned to the 37° C. humidified incubator with 5% $CO_2$ and carefully rocked every 30 minutes and after 3 hours of incubation, the mixture was removed and 4 mL fresh complete media medium was added to each dish. The supernatants were collected about 48 hours and again at 60 hours after transfection and were filtered through a 0.45 µm filter. The medium were aliquoted and stored in −80° C. until use. Infection of NIH3T3 cells with AXL retroviruses to generate stable NIH3T3/AXL cell lines: The NIH3T3 cells seeded in 10 cm culture dishes were changed to 4.5 mL of the collected medium containing AXL retroviruses plus freshly added polybrene (final concentration of 8 µg/mL). Six to eight hours later, 6 mL of complete DMEM medium was added into each culture dish and the cells were incubated with the medium for 48 hours. The cells were 1:4 split, and then selected with 0.5 µg/mL puromycin until all the uninfected NIH3T3 cells had died. The cells were then expanded and AXL expression and tyrosine phosphorylation in cells were confirmed by immunoblotting prior to in vivo xenograft studies.

Female Scid/Beige mice (6-8 weeks, Taconic, Hudson, N.Y.) were maintained 5/cage in microisolator units on a standard laboratory diet (Teklad Labchow, Harlan Teklad, Madison, Wis.). Animals were housed under humidity- and temperature-controlled conditions and the light/dark cycle was set at 12-hour intervals. Mice were quarantined at least 1 week prior to experimental manipulation. All animal studies were conducted under protocol #03-023 approved by the Institutional Animal Care and Use Committee (IACUC) of Teva Pharmaceuticals Inc.

NIH3T3/AXL cells were collected and resuspended in DMEM medium at density of $5\times10^7$/mL. An aliquot (100 µL) of the cell suspension ($5\times10^6$ cells) was inoculated subcutaneously to the left flank of each mouse with a 23 g needle. The mice were monitored and the tumor sizes were measured. When the NIH3T3/AXL tumor volumes reached 300 mm$^3$, the tumor-bearing mice were randomized into different treatment groups (8-10 mice/group) and were administered either vehicle (PEG-400) or CEP-40783 formulated in PEG-400 at indicated doses, qd, with 100 µL per dosing volume. The length (L) and width (W) of each tumor were measured with a vernier caliper and the mouse body weight was determined every two to three days. Tumor volumes were calculated with the formula of 0.5236*L*W*(L+W)/2. Statistical analyses of tumor volumes and mouse body weights were carried out with the Mann-Whitney Rank Sum Test. Plasma and tumor samples were obtained at 2 hours post final dose at each dose level, and the compound levels in plasma and tumor lysates were measured by LC-MS/MS.

Figure 4:
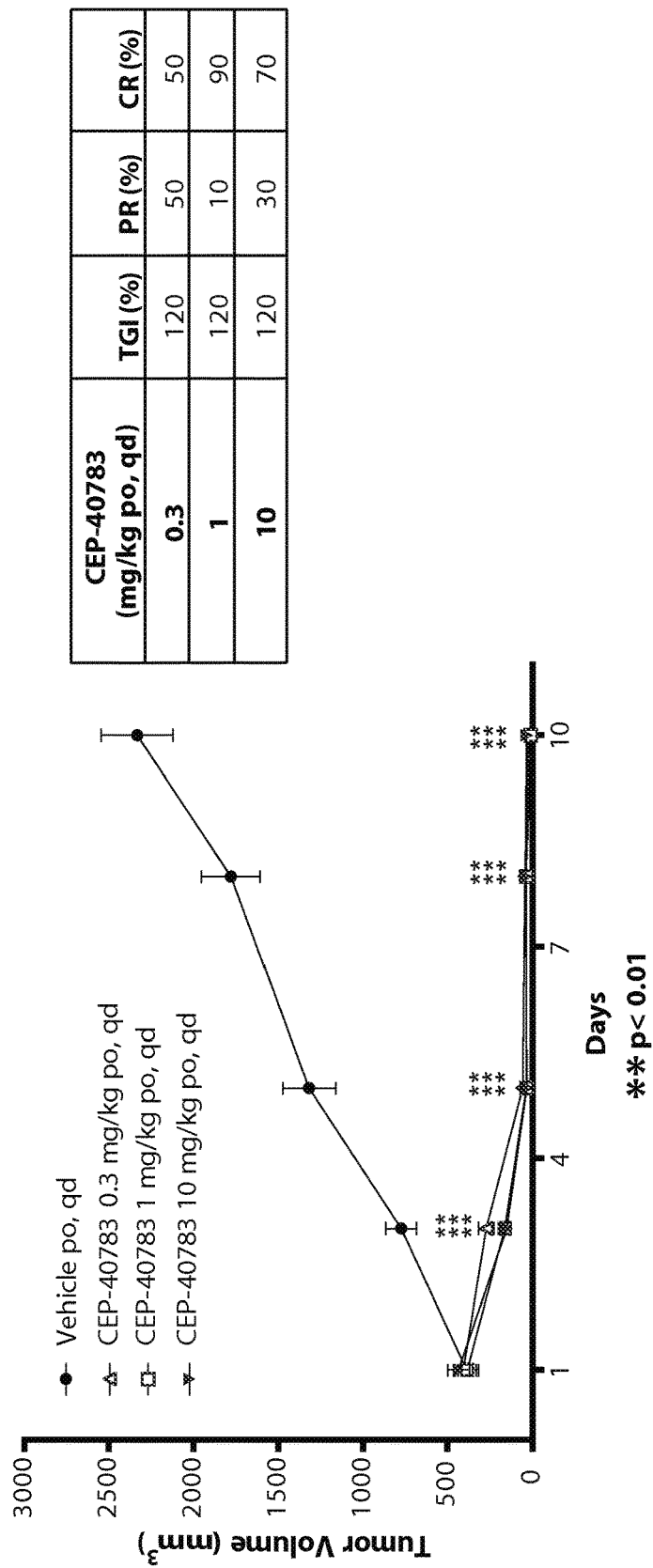
FIG. 4 depicts the anti-tumor efficacy of orally administered CEP-40783 in NIH3T3/AXL tumor xenografts in female SCID mice.

As shown in FIG. 4 female SCID mice bearing subcutaneous NIH3T3-AXL tumor xenografts were administered either vehicle or CEP-40783 at the following doses: 0.3 mg/kg, 1 mg/kg, or 10 mg/kg) by mouth (PO/per os), once a day (qd). Tumor sizes and mouse body weights were measured and recorded every two to three days and the absolute tumor volumes were calculated. Administration of CEP-40783 resulted in complete tumor regressions at all doses tested which is consistent with sustained and significant pharmacodynamic inhibition of AXL activity in these AXL-dependent tumors.

CEP-40783 Inhibits the Growth of GTL-16 Gastric Carcinoma Xenografts

The human gastric cancer cell line, GTL-16 was purchased from ATCC (American Tissue Culture Collection, Manassas, Va.) and cultured in DMEM medium with 10% fetal bovine serum (FBS, Cat# SH3007003, Hyclone Laboratory Inc, Logan, Utah). Female Nu/Nu mice (6-8 weeks, Charles River Laboratory, Wilmington, Mass.) were maintained 5/cage in microisolator units on a standard laboratory diet (Teklad Labchow, Harlan Teklad, Madison, Wis.). Animals were housed under humidity- and temperature-controlled conditions and the light/dark cycle was set at 12-hour intervals. Mice were quarantined at least 1 week prior to experimental manipulation. Experiments were approved (Protocol 03-023) by the Institutional Animal Care and Use Committee of Teva Pharmaceuticals Inc. GTL-16 cells were collected and resuspended in DMEM medium at density of $5\times10^7$/mL and an aliquot (100 µL) of the cell suspension ($5\times10^6$ cells) was inoculated subcutaneously to the left flank of each mouse with a 23 g needle. The mice were then monitored daily. When tumor volumes were approximately 200 mm$^3$, mice were randomized into different treatment groups (8-10 mice/group) and administered orally either vehicle (PEG-400) or CEP-40783 formulated in PEG-400 at indicated doses, qd, with 100 µL per dosing volume. The length (L) and width (W) of each tumor was measured with a vernier caliper and the mouse body weight was determined every 2-3 days. The tumor volumes were then calculated with the formula of 0.5236*L*W*(L+W)/2. Statistical analyses of tumor volumes and mouse body weight were carried out using the Mann-Whitney Rank Sum Test. **p<0.01 vehicle as compared to CEP-40783 treated groups. Plasma and tumor samples were obtained at 2 hours post final dose at each dose level, and the compound levels in plasma and tumor lysates were measured by LC-MS/MS. The TGI values were calculated at the end of study by comparing the tumor volumes (TV) of each CEP-40783-treatment group with those of vehicle-treated group with the following formula: 1-(the last day TV of compound-treated group/the last day TV of vehicle-treated group).

Figure 5:
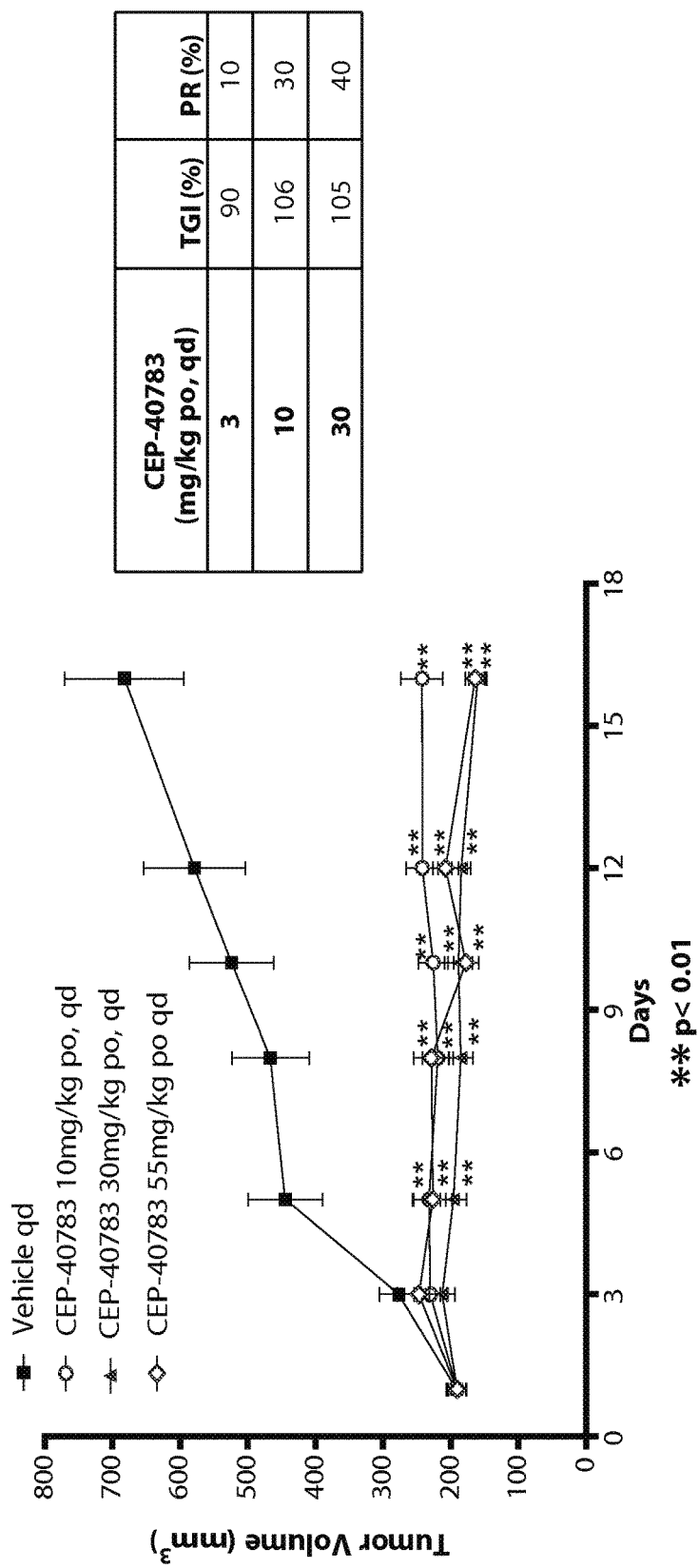
FIG. 5 depicts the anti-tumor efficacy of orally administered CEP-40783 in GTL-16 gastric carcinoma xenografts in female athymic nude mice.

These data (FIG. 5) demonstrate that oral administration of CEP-40783 results in significant anti-tumor efficacy (tumor stasis and regressions) at 10 and 30 mg/kg in this cMet-dependent tumor model.

CEP-40783 Inhibits the Growth of EBC-1 NSCLC Xenografts

The human NSCL cancer cell line, EBC-1 was purchased from ATCC (American Tissue Culture Collection, Manassas, Va.) and cultured in DMEM medium with 10% fetal bovine serum (FBS, Cat# SH3007003, Hyclone Laboratory Inc, Logan, Utah). Female Nu/Nu mice (6-8 weeks, Charles River Laboratory, Wilmington, Mass.) were maintained 5/cage in microisolator units on a standard laboratory diet (Teklad Labchow, Harlan Teklad, Madison, Wis.). Animals were housed under humidity- and temperature-controlled conditions and the light/dark cycle was set at 12-hour intervals. Mice were quarantined at least 1 week prior to experimental manipulation. Experiments were approved (Protocol 03-023) by the Institutional Animal Care and Use Committee of Teva Pharmaceuticals Inc. GTL-16 cells were collected and resuspended in DMEM medium at density of $5 \times 10^7$/mL and an aliquot (100 μL) of the cell suspension ($5 \times 10^6$ cells) was inoculated subcutaneously to the left flank of each mouse with a 23 g needle. The mice were then monitored daily. When tumor volumes were approximately 250 mm$^3$, mice were randomized into different treatment groups (8-10 mice/group) and administered orally either vehicle (PEG-400) or CEP-40783 formulated in PEG-400 at indicated doses, qd, with 100 μL per dosing volume. The length (L) and width (W) of each tumor was measured with a vernier caliper and the mouse body weight was determined every 2-3 days. The tumor volumes were then calculated with the formula of 0.5236*L*W*(L+W)/2. Statistical analyses of tumor volumes and mouse body weight were carried out using the Mann-Whitney Rank Sum Test. **$p<0.01$ vehicle as compared to CEP-40783 treated groups. Plasma and tumor samples were obtained at 2 hours post final dose at each dose level, and the compound levels in plasma and tumor lysates were measured by LC-MS/MS. The TGI values were calculated at the end of study by comparing the tumor volumes (TV) of each CEP-40783-treatment group with those of vehicle-treated group with the following formula: 1-(the last day TV of compound-treated group/the last day TV of vehicle-treated group).

Figure 6:
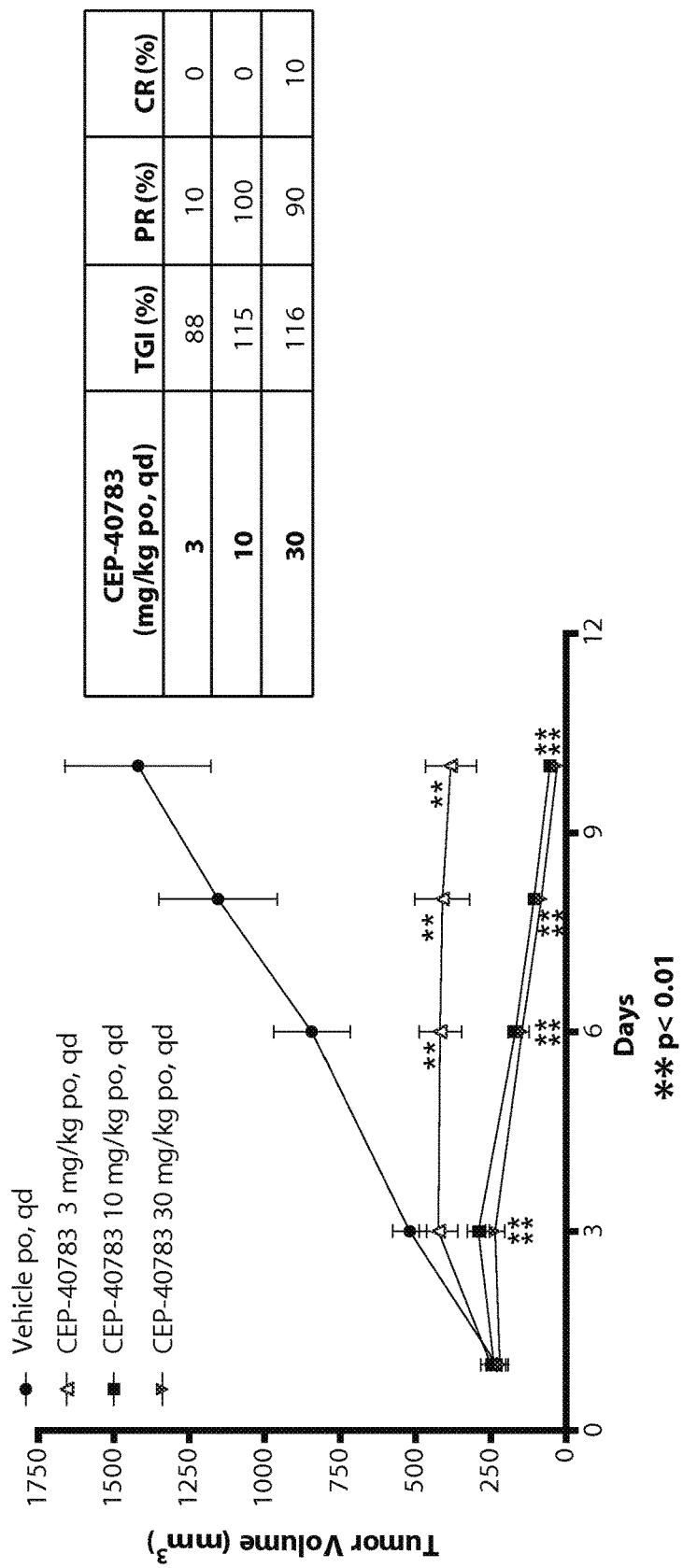
FIG. 6 depicts the anti-tumor efficacy of orally administered CEP-40783 in EBC-1 Human NSCLC xenografts in female athymic nude mice.

As shown in FIG. 6, oral administration of CEP-40783 at doses of 10 mg/kg and 30 mg/kg resulted in tumor regressions, with tumor stasis and partial regressions observed at 3 mg/kg in this c-Met dependent tumor model.

Discontinuous and Alternate Oral Dosing Schedules of CEP-40783 Maintain Significant Anti-Tumor Efficacy Similar methods to those described above for FIG. 6 were employed to evaluate the anti-tumor effects of discontinuous and alternate oral dosing schedules of CEP-40783. Upon EBC-1 tumor xenografts reaching approximately 200 mm$^3$, mice were randomized into different treatment groups (8-10 mice/group) and administered orally either vehicle (PEG-400) or CEP-40783 formulated in PEG-400 at 10 mg/kg qd. After a period of 7 days of continuous dosing, animals were then switched to either a 7 day on/7 day off 10 mg/kg qd dosing regimen, or intermittent twice weekly (q2d) or thrice weekly (q3d) oral dosing at a 10 mg/kg qd dose for a total of 21 days.

Figure 7:
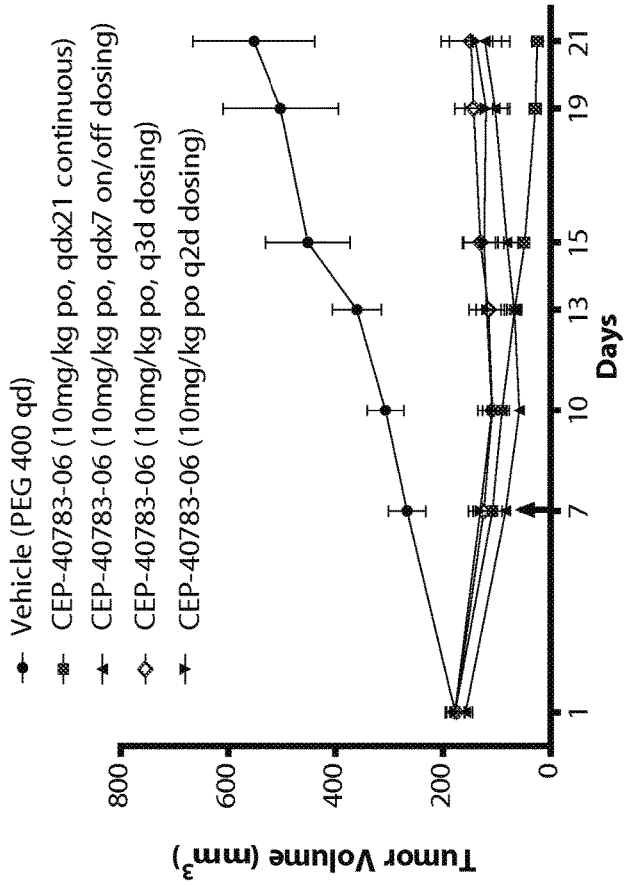
FIG. 7 depicts the effects of different dosing schedules of CEP-40873 on growth of EBC-1 Human NSCLC xenografts.

As seen in FIG. 7 significant anti-tumor efficacy is maintained when CEP-40783 is dosed orally for 7 days followed by dosing holidays (qd×7, dosing every 7 days) and/or alternate dose schedules, i.e., q3d (dosing every three days) or q2d (dosing every two days). Specifically, partial responses were seen in groups that were dosed orally with CEP-40783 every 7 days (40%) every 3 days (70%) and every 2 days (40%). Complete tumor regressions were seen in 10% and 20% of animals in the qd×7 and q2d dosing groups, respectively, which is indicative that discontinuous and intermittent dosing of CEP-40783 retains highly significant anti-tumor activity consistent with its tumor pharmacodynamic profile.

CEP-40783 Inhibits 4T1-Luc2 Systemic Dissemination

The murine breast cancer cell line 4T1-luciferase tagged cell line generated by stable transfection of the firefly luciferase gene expressed from the SV40 promoter was purchased from Caliper Life Sciences. The cells were grown in DMEM medium supplemented with 10% fetal bovine serum (FBS, Cat$^{\#}$ SH3007003, Hyclone, Logan, Utah). D-Luciferin firefly/potassium salt (Cat. # L-8220) was purchased from Biosynth International, Inc., Itasca, Ill.). Female Balb-c mice (6-8 weeks) were purchased from Charles River laboratories. The Balb/c mice were injected with $0.5 \times 10^5$ 4 T1-Luc2 cultured tumor cells iv (tail vein) two days after the start of treatments with either PEG-400 or CEP-40783 formulated in PEG-400 (dosed at 1, 10 and 30 mg/kg, po, qd). Two days later, the mouse body weights were measured twice a week and the mice were subjected for full body in vivo imaging thrice a week. Treatments were given for a total of 23 days, with 21 days post tumor cell seeding. Bioluminescence image analysis was performed at the end of the study using a Caliper Life Sciences (Xenogen) Spectrum in vivo imaging machine. Each cage of five mice was anesthetized using isofluorane and imaged for a series of time points from 0.5-5 minutes max. Image analysis was performed using Living Image Software (vs. 4.0, 2010) using subjective but equally sized gates or regions of interest (ROIs) overlaid on each animal image. Counts were converted to average radiance or mean photon flux; expressed as photons per second per cm2 of surface area, (p/s/cm2/sr). Mann-Whitney non-parametric, 1- or 2-way ANOVA were used as statistical tests, a p-value less than 0.05 were considered significant. Statistical software used was Graph Pad Prism (vs. 5.01, 2007), and calculations were performed using Microsoft Office Excel (Professional, 2003).

Figure 8:
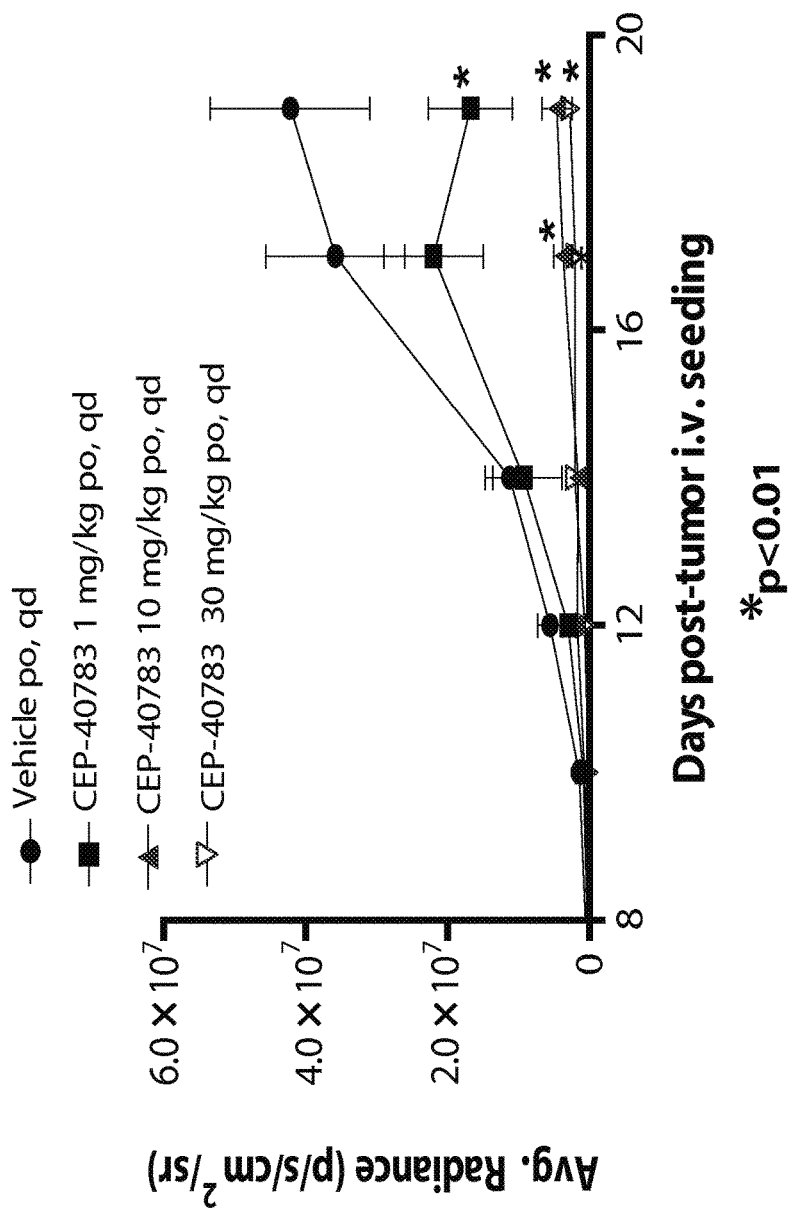
FIG. 8 depicts the anti-tumor effects of orally administered CEP-40783 in female Balc/c mice implanted (i.v.) with 4T1-Luc2 murine mammary carcinoma cells.

As seen in FIG. 8 oral administration of CEP-40783 results in highly significant reductions in systemic 4T1 mammary tumor dissemination at the 10 mg/kg and 30 mg/kg doses, and a significant, albeit of lesser magnitude, reduction in tumor dissemination at the 1 mg/kg dose as well.

CEP-40783 Decreases Lymph Node Metastases of MDA-MB-2312 Leu Orthotopic Breast Cancer Implants The human breast cancer cell line MDA-MB-231-Leu-D3H2LN-luciferase expressing cell line was purchased from Caliper Life Sciences. This tumor cell line was generated by stable transfection of the firefly luciferase gene expressed from the SV40 promoter and further selected for its metastatic potential upon isolation from a spontaneous lymph node metastasis of MDA-MB-231-Luc cells in immune-compromised mice. The cells were grown in DMEM medium supplemented with 10% fetal bovine serum (FBS, Cat$^{\#}$ SH3007003, Hyclone, Logan, Utah). D-Luciferin firefly/potassium salt (Cat. # L-8220) was purchased from Biosynth International, Inc., Itasca, Ill.). Female nu/nu mice (6 to 8 weeks old) were purchased from Harlan Laboratories. MDA-MB-231-luc-D3H2LN ($2 \times 10^6$) cells were implanted orthotopically into the mammary fat pad of nu/nu mice and two days later, the mice were grouped (10 mice per group) and orally administered either vehicle (PEG-400) or CEP-40783 formulated in PEG-400 at 10 and 30 mg/kg qd. Mouse body weights were measured on day 0 and then every 7 days, and bioluminescence image analysis performed at the end of the study using the Caliper Life Sciences (Xenogen) Spectrum imager as detailed in FIG. 6. Images of the primary tumor and potential metastatic tumors in lymph nodes were taken weekly, starting on day 7 post cell implantation. Prior to image acquisition, each mouse were give a 0.2 ml intra-peritoneal injection of D-Luciferin firefly/potassium salt and images were acquired 6-10 minutes post substrate administration. The primary tumors were covered with electrical tape or thick black paper to avoid interference in imaging metastatic tumors residing in lymph nodes. The mice with bioluminescent images disseminated into peritoneal cavity on the first imaging were discarded. The study ended when the bioluminescent signals from the primary tumors became too strong to effectively assess the detection of metastatic tumors in lymph nodes. At the end of study, the mice were sacrificed and the plasma and primary tumors were collected for LC/MS analysis. Image analyses was performed after all the images had been taken, using Living Image Software (vs. 4.0, 2010). Counts were converted to average radiance or mean photon flux; expressed as photons per second (p/s).

Figure 9:
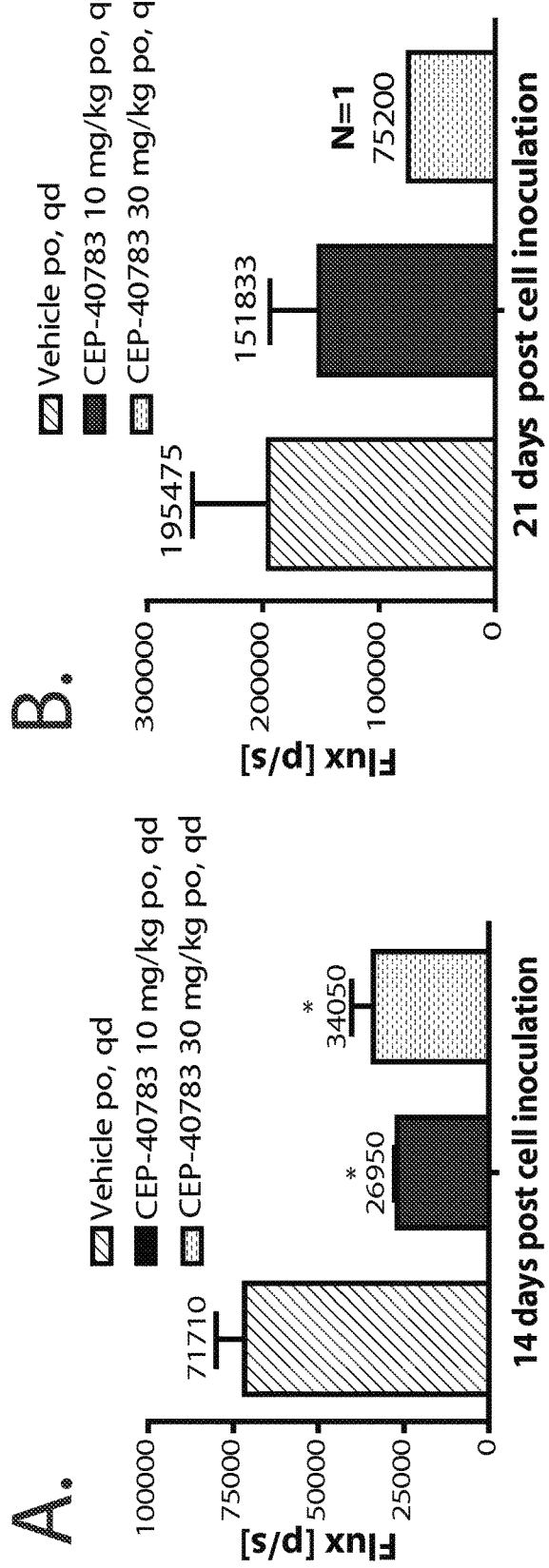
FIGS. 9A and 9B depict the effect of oral administration of CEP-40783 on metastases of MDA-MB-231-Leu orthotopic breast tumor xenografts in female nude mice.

FIG. 9A shows the quantitation of radiance values in primary tumors on Day 14 post inoculation. FIG. 9B shows quantitation of radiance values on Day 21 post-inoculation for lymph node metastases. Values represent mean±SEM of radiance values. Statistical analyses were performed using Mann-Whitney Rank Sum Test or 1- or 2-way ANOVA for significance differences between treatment groups. *p<0.05-vehicle as compared to CEP-40783 treated. These data (FIGS. 8, 9A and 9B) show that oral administration is efficacious in reducing spontaneous lymph node and pulmonary metastatic tumor burden in these models.

AXL/c-Met Dual Inhibition: Therapeutic Utility

AXL and c-Met activation are estimated to be the underlying mechanism(s) responsible for the acquisition of anti-EGFR resistance in up to 50% of EGFR-mutated NSCLC patients. Other cancer types with a high prevalence of constitutive AXL and/or c-Met activation include: breast cancer, non-small cell lung cancer (NSCLC), pancreatic cancer, gastric cancer, esophageal cancer, and ovarian cancer.

Table 2 (below) summarizes the results of a number of experiments where CEP-40783 has demonstrated efficacy in a number of erlotinib-insensitive NSCLC models and has shown superiority to an optimal paclitaxel dosing regimen.

TABLE 2

| | | % Tumor Growth Inhibition | | |
| --- | --- | --- | --- | --- |
| Model Name | Study Duration (days) | CEP-40783 10 mg/kg po/qd | CEP-40783 30 mg/kg po/qd | Paclitaxel 10 mg/kg iv/q4dx3 |
| CTG-0157 | 14 | 3% | 85%*† | 41% |
| CTG-0165 | 37 | 116%*† | 118%*† | 56%* |
| CTG-0159 | 14 | 46%* | 66%*† | 25%* |
| CTG-0170 | 10 | 104%*† | 107%*† | 77%* |
| CTG-0192 | 32 | 85%* | 71%* | 105%* |

Data from CTG-0157 and CTG-0159 is on file but not included here.
*Indicates statistical significance (P < 0.05) compared to the control group.
†Indicates statistical significance (P < 0.05) compared to the group treated with paclitaxel.

As shown in Table 2 oral administration of CEP-40783 results in significant efficacy (TGI and/or tumor regression) in all human primary NSCLC TumorGrafts. CTG-0192 is an erlotinib-sensitive model which was found to be the least CEP-40783 sensitive tumor relative to paclitaxel.

Efficacy in Erlotinib-Insensitive Primary NSCLC Human TumorGrafts™

Figure 10:
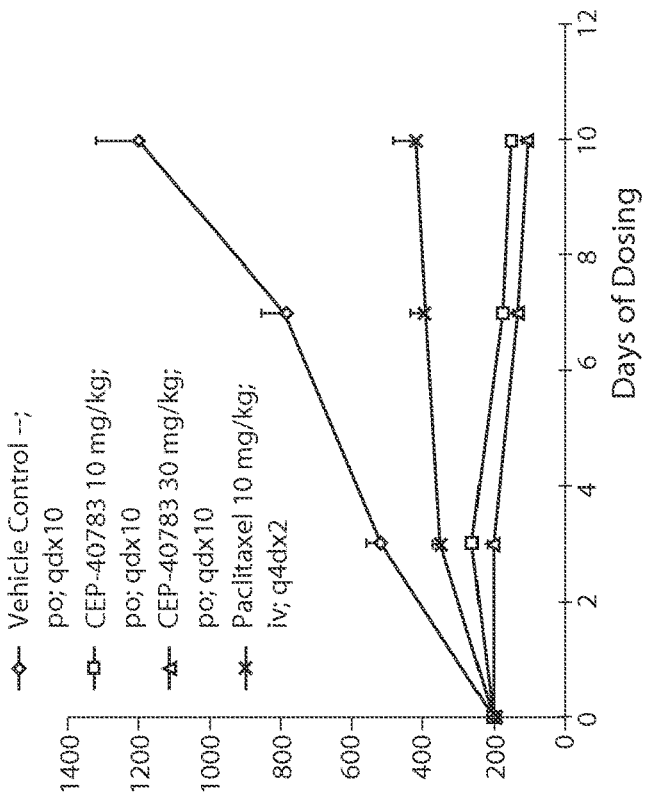
FIG. 10 depicts the effects of oral administration of CEP-40783 in erlotinib-insensitive primary NSCLC human TumorGraphs™.
Figure 10:
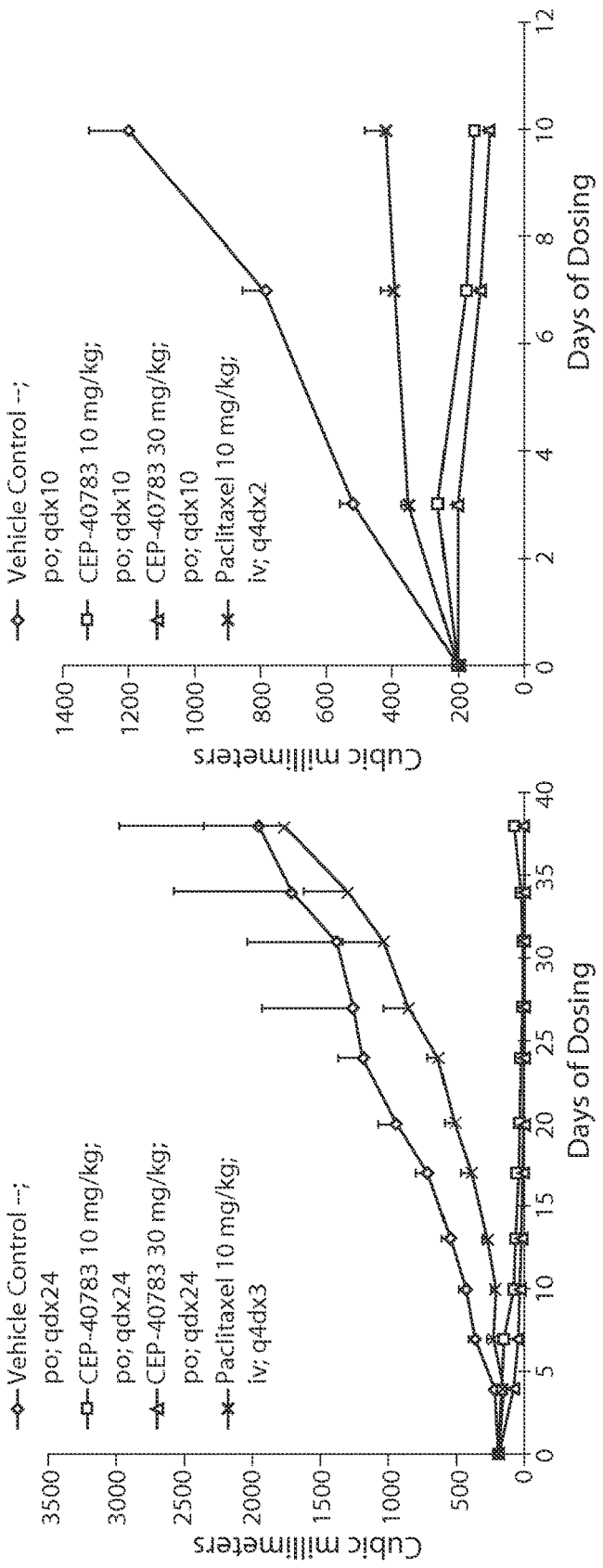

FIG. 10 presents data from two erlotinib-insensitive human TumorGraft models (CTG-0165 and CTG-0170). AXL and/or c-Met are constitutively activated in these models and, as shown, oral CEP-40783 demonstrates superior efficacy in both models as evidenced by tumor regressions at the 10 mg/kg and 30 mg/kg doses relative to standard of care (SoC) therapy, namely paclitaxel 10 mg/kg, iv, q4dx2).

Figure 11:
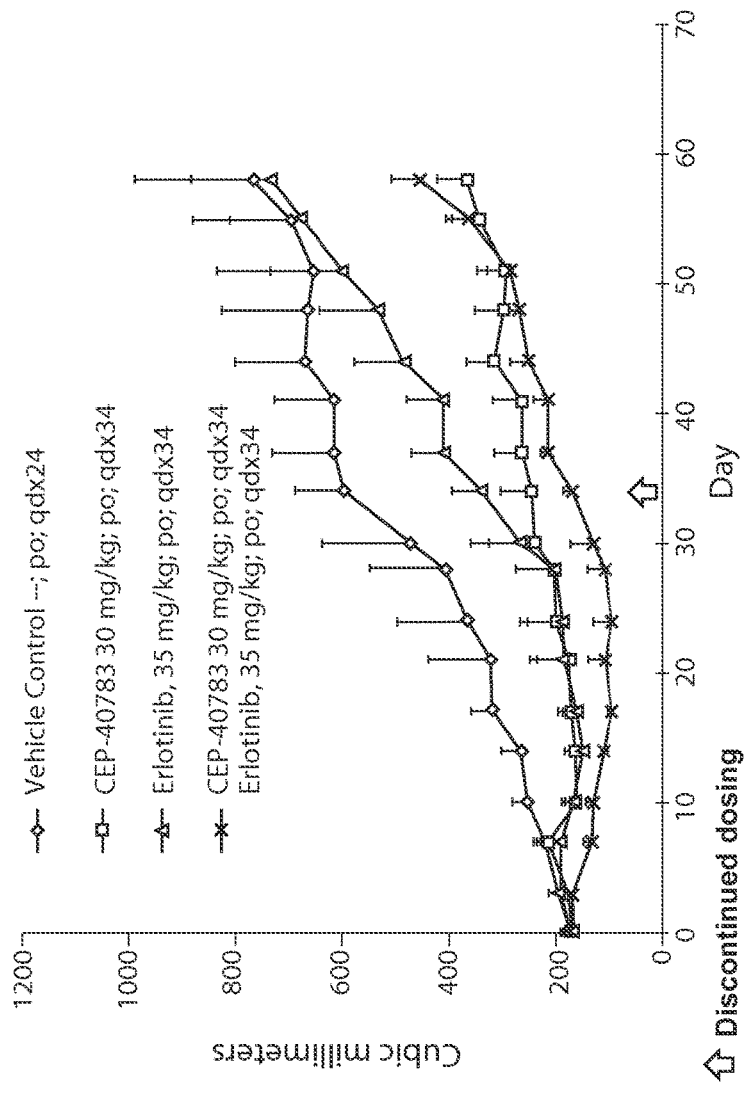
FIG. 11 depicts the activity of CEP-40783 and erlotinib in "erlotinib-sensitive" NSCLC TumorGraft™ having activated AXL and c-Met.

Activity of CEP-40783 and Erlotinib in "Erlotinib-Sensitive" NSCLC TumorGraft™ with Activated AXL and c-Met FIG. 11 presents data from an erlotinib-sensitive NSCLC TumorGraft™ model (CTG-0192) with activated AXL and c-Met. As seen in the graph (FIG. 11), in the animals dosed with erlotinib (35 mg/kg, po, qdx34) there was initial sensitivity followed by acquired erlotinib-resistance at (approx.) day 29. Dosing was discontinued at day 34. Moreover, upon discontinuation of dosing, the rate of tumor regrowth was similar to control/vehicle.

Tumor regressions were achieved in the combination treatment group (CEP-40783/erlotinib) and in the group treated with CEP-40783 as a single agent significant TGI/tumor stasis was maintained even after dosing was discontinued (day 34).

Unlike erlotinib, there was no acquired resistance to CEP-40783 during the treatment phase of the experiment. In addition, there was a long-lasting anti-tumor effect in the CEP-40783 (alone) group even after discontinuation of treatment.

Methods (for the experiments shown in FIGS. 10 and 11)

Female immunocompromised nu/nu mice (Harlan) between 6-9 weeks of age were housed on irradiated papertwist-enriched ⅛" corncob bedding (Sheperd) in individual HEPA ventilated cages (Innocage® IVC, Innovive USA) on a 12-hour light-dark cycle at 68-74° F. (20-23° C.) and 30-70% humidity. Animals were fed water ad libitum (reverse osmosis, 2 ppm Cl2) and an irradiated Test rodent diet (Teklad 2919) consisting of 19% protein, 9% fat, and 4% fiber.

Tumor Models: Champions TumorGraft models of NSCLC are owned by Champions Oncology. In this study, animals were implanted unilaterally on the right flank with tumor fragments harvested from host animals. When tumors reached approximately 150-250 $mm^3$, animals were matched by tumor volume into treatment and control groups and dosing initiated (Day 0); mice were ear-tagged and followed individually throughout the experiment.

CEP-40783 was formulated using vehicle components (PEG400) supplied by Champions. Erlotinib (manufacturer: OSI Pharmaceuticals; National Drug Code: 50242-062-01; Lot #: US0002) was formulated using 100% PEG-400 as the vehicle according to manufacturer's specifications.

Efficacy measurements: Beginning Day 0, tumor dimensions were measured twice weekly by digital caliper (Fowler Ultra-Cal IV) and data including individual and mean estimated tumor volumes (Mean TV±SEM) were recorded for each group; tumor volume was calculated using the formula TV=$width^2 \times length \times 0.52$. At study completion, percent tumor growth inhibition (% TGI) values were calculated and reported for each treatment group (T) versus control (C) using initial (i) and final (f) tumor measurements by the formula: % TGI=$1-T_f-T_i/C_f-C$; single agent or combination therapies resulting in a TGI>50 at study completion are considered active in the tested model at the evaluated treatment regimen according to NCI guidelines. Individual mice reporting a tumor volume ≤50% of the Day 0 measurement for two consecutive measurements over a seven day period were considered partial responders (PR). If the PR persisted until study completion, percent tumor regression (% TR) was determined using the formula: % TR=$1-T_f/T_i \times 100$; a mean value was calculated if multiple PR mice occurred in one group. Individual mice lacking palpable tumors (<4×4 mm$^2$ for two consecutive measurements over a seven day period) were classified as complete responders (CR); a CR that persisted until study completion was considered a tumor-free survivor (TFS). TFS animals are excluded from efficacy calculations. Statistical differences in tumor volume were determined using a two-tailed One-Way Analysis of Variance (ANOVA) followed by the Dunett's multiple comparisons test comparing treated groups with control and combinations with standard agent alone when possible. All data collected in this study was managed electronically and stored on a redundant server system.

The data described herein clearly demonstrates that CEP-40783 exhibits potent AXL and c-Met pharmacodynamic and anti-tumor efficacy in established tumor xenograft models. In all of the above studies CEP-40783 was well tolerated with no compound-related body weight loss. As such, CEP-40783 may have potential therapeutic utility in multiple human tumor types in which c-Met and AXL activity play a critical role in tumor formation, local invasion and metastasis. The data further suggests that CEP-40783 can be used as adjuvant/neoadjuvant therapy in combination with standard of care chemotherapies to enhance overall efficacy and/or to limit or prevent metastatic dissemination of the primary tumor (resectable or non-resectable).

What is claimed is:

1. A method of treating a cancer in a subject, comprising (a) administering to the subject a first compound selected from erlotinib and gefitinib until the cancer exhibits resistance to said first compound, then (b) administering to the subject a combination of (i) the first compound selected from erlotinib and gefitinib, and (ii) a second compound which is or a pharmaceutically acceptable salt thereof, wherein said cancer is selected from non-small cell lung cancer (NSCLC), breast cancer, gastric cancer, and pancreatic cancer.

2. The method of claim 1, wherein the second compound, or a pharmaceutically acceptable salt thereof is administered to the subject from one to four times daily.

3. The method of claim 2, wherein the second compound, or a pharmaceutically acceptable salt thereof, is administered to the subject in an amount from about 10 mg/kg to about 55 mg/kg.

4. The method of claim 1, wherein the cancer is NSCLC.

5. The method of claim 1, wherein said cancer is breast cancer.

6. The method of claim 1, wherein said cancer is gastric cancer.

7. The method of claim 1, wherein said cancer is pancreatic cancer.

8. The method of claim 1, wherein said cancer is non-small cell lung cancer.

* * * * *